United States Patent
Studin

(12) 
(10) Patent No.: US 6,337,076 B1
(45) Date of Patent: Jan. 8, 2002

(54) METHOD AND COMPOSITION FOR THE TREATMENT OF SCARS

(75) Inventor: Joel R. Studin, Great Neck, NY (US)

(73) Assignee: SG Licensing Corporation, Great Neck, NY (US)

(*) Notice: Subject to any disclaimer, the term of this patent is extended or adjusted under 35 U.S.C. 154(b) by 0 days.

(21) Appl. No.: 09/441,138

(22) Filed: Nov. 17, 1999

(51) Int. Cl.$^7$ .................................................. A61K 6/00
(52) U.S. Cl. .................. 424/401; 428/78.03; 428/78.05; 428/78.06; 428/78.07; 514/817; 514/887
(58) Field of Search ................................ 424/401, 78.03, 424/78.05, 78.06, 78.07; 514/817, 887

(56) References Cited

U.S. PATENT DOCUMENTS

| | | |
|---|---|---|
| 4,226,858 A | 10/1980 | Pfirrmann et al. |
| 4,645,668 A | 2/1987 | Pinnell |
| 5,128,375 A | 7/1992 | Tanaka et al. |
| 5,534,246 A | 7/1996 | Herb et al. |
| 5,552,162 A | 9/1996 | Lee |
| 5,702,694 A | 12/1997 | Chamness |
| 5,874,074 A | 2/1999 | Smith |
| 5,885,581 A | 3/1999 | Massand |
| 5,891,076 A | 4/1999 | Fabo |
| 5,895,656 A | 4/1999 | Hirshowitz et al. |
| 5,919,476 A | 7/1999 | Fischer et al. |

FOREIGN PATENT DOCUMENTS

| | | | |
|---|---|---|---|
| PT | BR 970684 | * | 10/1999 |
| RU | SU 1540830 | * | 2/1990 |

OTHER PUBLICATIONS

"The Merck Index" Published by Merck Research Labs., Div. of Merck —Co., Inc., 1996, pp. 420–421.

* cited by examiner

*Primary Examiner*—S. Mark Clardy
*Assistant Examiner*—Michael A. Williamson
(74) *Attorney, Agent, or Firm*—Stuart D. Frenkel; Liniak, Berenato, Longacre & White

(57) ABSTRACT

A method and composition for treating hypertrophic scars so as to reduce the size and approve the appearance of scars comprises applying to the scar a composition comprising a film-forming carrier such as a Collodion which contains one or more active ingredients such as a topical steroid, silicone gel and vitamin E. Novel compositions using the Collodion film-forming carrier are also useful to treat a variety of adverse skin disorders.

24 Claims, No Drawings

METHOD AND COMPOSITION FOR THE TREATMENT OF SCARS

FIELD OF THE INVENTION

This invention relates to a method for the treatment of scars and, in particular, to a method for improving the size and appearance of scar tissue. The invention also relates to a novel topical composition for treatment of scars and other skin conditions and diseases.

BACKGROUND OF THE INVENTION

When skin or dermis has been traumatized by cutting or burning, scar tissue is formed. In most cases, a small cut or burn area will result in a correspondingly small amount of scar tissue which is not readily discernable to a casual observer. In other cases, where the traumatized area is large and/or lengthy, scarring and scar tissue are quite apparent to a casual observer. This cannot only be embarrassing for the person who is scarred, but can be a distraction for the casual observer. The problem is compounded when, over time, scar tissue tends to darken, become thick and project outwardly from the skin surface, thus becoming more apparent.

In normal wound-healing or sore-healing processes, the abundant vascular network is regenerated in the wound or the sore during the maturing phase and the collagen fibers collect in large bundles. Changing patterns of the connective tissue matrix during growth, development, and repair during the healing if a wound and sore require a delicate balance between the synthesis and degradation of collagen. Under normal circumstances, the balance between the synthesis and degradation of collagen is maintained. However, sometimes this maturing process fails to occur, so that scar tissue remains beneath the covering epithelium for a relatively long period of time and may even develop and become enlarged. This is the clinical nature of a hypertrophic scar.

Although balanced scar formation and remodeling are essential processes in skin wound healing, disorders of excess scar formation remain a common and therapeutically refractory clinical problem. A hypertrophic scar is an excessive scar which by definition has grown in size beyond that required for normal wound healing. Hypertrophic scars can emerge from many wound types, such as from a burn or a sharp incision. A hypertrophic scar is a raised, red and itching enlargement. The scar may be tender to the touch and to other external pressure and can form on every afflicted part of the body.

Hypertrophic scars often remain for a very long time, sometimes through the entire life of the person so afflicted. In the case of adults, the hypertrophic scar will normally transform to a typical soft and pale scar after a year or so. In addition to itching and being relatively unsightly, if the hypertrophic scar happens to overlay a skeletal joint, movement of the joint is often painful and restricted. In the past, such complications were overcome by covering the scar tissue with clothing, makeup, or avoiding contact with other people. This strategy is often not possible nor desirable. Scar tissue and the tissue adjacent thereto can often become hyper-sensitive to contact with clothing, and often, a person will not cover the scar tissue to the detriment of socialization. In some instances, a person might not be able to tolerate the application of makeup over scar tissue, again to the detriment of socialization. In other instances, a person may be required to wear a certain type or style of clothing which does not cover scar tissue locations.

Many medical care givers have recognized the problems associated with scar tissue and now include scar tissue management as part of the overall treatment of patients.

A number of techniques have been proposed for the improvement of scars. These include the application of pressure and treatments such as with hydrocortisone, collagen, vitamins such as vitamins E and A, and extracts from vegetable and animal sources. While some of these treatments have had modest success, all of the treatments can be cumbersome, inconvenient or even painful.

The use of pressure dressings is believed to be the first truly effective scar treatment. Application of pressure apparently increases the activity of collagenase, which is an enzyme capable of degrading and modeling the scar tissue and is employed by the body in the equilibrium of the formation and degradation of collagen during the healing process. However, pressure dressings are bulky rendering them uncomfortable to the user and often inconvenient to keep in place on the affected scar tissue.

The application of a steroid such as cortisone also increases the collagen degradation activity of collagenase. With a large amount of extra scar tissue such as a hypertrophic scar or keloid, depending on the severity, a physician often recommends cortisone injections. In less severe cases, cortisone creams or cortisone tapes do show modest benefit. However, creams are often inconvenient to use as they are messy and can stick to and discolor clothing. The use of tapes are also disadvantageous as such tapes often hold moisture and fall off the affected area. Further, the cortisone creams are required to be rubbed or massaged onto the scar. For some persons, this can be painful. Cortisone injections can also be very painful to the patient.

Vitamin treatment such as vitamin E is believed to decrease the collagen bonding during the wound healing process and has been used to soften scars. Cutting vitamin E gelatin capsules in half and squeezing out the oil has been the most common way to apply vitamin E to wounds. Obviously, a vitamin E oil is messy and cutting the capsules in half is a tedious process. The addition of vitamins A and E in creams and lotions is also known, but such creams and lotions are often oily to the touch and do not dry so as to remain in an oily condition or take a long period of time to rub completely into the skin. Again, rubbing or massaging a cream or oil onto and/or into certain scar tissue can be painful to some persons.

It has been discovered in recent years that the shrinkage of hypertrophic scars can be increased by applying silicone-gel plates or sheets to the scars. The exact mechanism by which the silicone-gel interacts with such scars has not been established, however. A number of products are available commercially for this purpose, for instance such products as Dow Corning Silastic Sheeting, Cica-Care (Smith & Nephew), Epi-Derm (Biodermis), Nagosil (Nagor), among others. These products have the form of molded silicone-gel sheets having a thickness of 2–4 millimeters. In treating hypertrophic scars, these sheets are placed over the scars and are worn for a relatively long period of time, often from 3–12 months, until the scars either have decreased or have regenerated. Examples of recent patents which disclose such silicone-gel sheets include U.S. Pat. Nos. 5,759,560; 5,891,076; 5,895,656 and 5,919,476.

The known silicone sheets are relatively rigid and after having been placed over the scar have insufficient adhesion to remain securely in position without some form of assistance. Consequently, it is necessary to secure the sheets against the skin with the aid of securing, stocking, bandage, self-adhesive tape or some like means. The sheets can often trap too much moisture causing irritation on the affected area. Additionally, gel sheets of the type that utilize silicone are tacky to the touch, both on the inner body, body contacting surface and the exterior surface. Having a body contacting surface which is tacky to the touch is advantageous and desirable. However, having an exterior which is tacky to the touch is not. A disadvantage of having a tacky exterior is that articles of clothing tend to adhere to the gel sheet. This presents several problems. One problem is that often the gel sheet adheres to an article of clothing with greater force than it adheres to the skin. Thus, when the article of clothing is removed, the gel sheet is removed from the body. Another problem is that the articles of clothing would adhere to the gel sheet and prevent normal range of motion. An additional problem encountered with gel sheets which are tacky to the touch is that they tend to become soiled more quickly.

Other physical treatments are available, including surgery, x-ray therapy and cryotherapy. Such treatments are expensive or potentially dangerous and not normally recommended.

Accordingly, while there have been physical treatments, compositions and/or articles which contain medicaments which have had modest success in reducing, softening and lightening hypertrophic scars, these prior attempts are expensive, inconvenient to use, difficult to apply or simply have not been very effective in achieving the desired purpose.

SUMMARY OF THE INVENTION

As expressed above, existing therapy for hypertrophic scars and keloids has included surgery, mechanical pressure, X-ray irradiation, cryotherapy, and the application of various medicaments such as steroids, vitamins, as well as vegetable and animal extracts. Again, there are many disadvantages associated with each of these methods. Thus, surgical removal of the scar tissue is often incomplete and can result in the development of hypertrophic scars and keloids at the incision and suture points. X-ray therapy is the only predictably effective treatment to date, however, because of its potential for causing cancer, X-ray therapy is not generally recommended or accepted. The most common approach to control hypertrophic scar and keloid formation is to apply pressure, which appears to be effective in many instances. However, this treatment has limited application, generally based on the size and location of the scar tissue on the body. Steroid injections are unpredictable and often result in depigmentation of the skin. Application of silicon-based gels such as in sheets has resulted in general improvement in the appearance and size of treated scars, but the mechanism of such healing is not known and the inconvenience of such silicone gel sheets has been discussed previously.

Accordingly, a primary objective of the present invention is to provide an effective and, yet convenient to use composition which can improve the size and appearance of scars, in particular, hypertrophic scars.

In its broadest aspect, the present invention is directed to a method for the treatment of hypertrophic scars with a medicament capable of reducing the size or improving the appearance of scars and which is carried within a film-forming carrier which can be accurately and directly applied to the affected scar tissue, and dries to a substantially clear film to hold the medicament in place. The film-forming carrier of the present invention is Collodion which comprises a solution of pyroxilin (nitrocellulose) in a 25/75 mixture of alcohol and ether, or Flexible Collodion which comprises a mixture of Collodion with camphor and castor oil. This film-forming carrier is not oily or greasy as has characterized carriers used with the application of vitamins or other vegetable or animal extracts or with steroids. The film-forming carrier of the present invention can be applied directly onto the scar to be treated without the need for rubbing or the application of pressure such as with oily or greasy carriers which application can often be painful to the person whose scar is being treated.

In another aspect of the present invention, a composition is provided which is effective for reducing the size and appearance of hypertrophic scars and can be readily and accurately applied directly to the scar without the problems associated with oils and greases, or wraps and sheets, which have been used to merely apply pressure or provide contact with silicon gels. In this aspect of the invention, a composition is provided comprising a Collodion or Flexible Collodion film-forming carrier which includes a dermatologically effective steroid such as a corticosteroid which can be applied directly onto the scar tissue and which dries to a clear film which contains the steroid medicament.

In an alternative to the invention described immediately above, a corticosteroid, silicone gel or vitamin E, or mixtures thereof is provided in a Collodion or Flexible Collodion film-forming carrier and used to treat not only scars but a variety of skin conditions and disorders.

In still another aspect of the present invention, a composition for the treatment of hypertrophic scars so as to reduce the size of the scar and improve the appearance thereof is provided by combining a dermatologically effective steroid such as hydrocortisone, a silicone gel and, optionally, vitamin E in a single carrier which can be applied directly to the scar tissue and presents for the first time a multicomponent medicament composition combining the effective properties of components which have been used singly. It has been found that the steroid, silicone gel and vitamin E can be effectively mixed within a film-forming carrier such as Collodion or Flexible Collodion and be applied directly to the scar tissue in a convenient manner without the need for massaging the composition into the scar. The composition dries to a clear film, remaining on the affected area without the need for wraps, tapes, and without the disadvantages of oils or greases which disadvantageously can discolor clothing and need to be rubbed or massaged onto and into the scar.

DETAILED DESCRIPTION OF THE INVENTION

The method of the present invention is directed to the application of a film-forming carrier to the affected scar tissue. The film-forming carrier contains one or more medicaments (active ingredients) which applied onto the scar tissue and held in place by the carrier film can reduce the size of a hypertrophic scar and/or improve the appearance thereof. Thus, the method of the present invention is the application of a film-former and one or more effective scar-treating medicaments to a hypertrophic scar. When the film-former dries, it forms a protective film over the site of application to maintain contact of the active ingredients on the scar and prevent removal of the active ingredients from the site. The film-former which is preferably used in the method of the present invention is Collodion or Flexible Collodion. Collodion is a solution of 4 g. of pyroxylin (chiefly nitrocellulose) in 100 ml of a mixture of 25 milliliters alcohol and 75 milliliters ether. Collodion is a colorless or slightly yellow, clear or slightly opalescent syrupy liquid. The flexible Collodion comprises simple Collodion with the addition of camphor and 3% castor oil (by weight). Flexible Collodion is slightly yellow and is a syrupy liquid which contains 67% ether and about 22% absolute alcohol by volume. When the Collodion or Flexible Collodion evaporates it leaves a tough and colorless film. The topical compositions of the invention may also contain a solvent added to the carrier which serves to dissolve the active ingredient. An example of a solvent which may be used is acetone.

In the method of this invention, an active ingredient which is effective to treat hypertrophic scars is included in the Collodion or Flexible Collodion film-forming carrier. Any active ingredient which is so effective, known or unknown at the present time, is useful in the method of this invention. Such active ingredients include dermatologically active steroids, e.g. corticosteroids, vitamins and other vegetable and animal extracts known to treat scars, as well as silicones, including silicone gels which have been used in silicone gel sheets and plates.

In preparing topical compositions for use in the method of this invention, there can be added conventional adjuvants such as propionic acid, propylene glycol, acetone and lactic acid, conventional penetration enhancers such as erucic acid, oleic acid and bahemic acid; conventional buffers, preservatives, hydrophilic emulsifiers, lipophilic emulsifiers, sun-screening agents, perfumes, emollients, deodorants, humectants, and the like. Colorants may also optionally be added in the useful compositions of the invention. obviously, adjuvants which would be harmful to scar tissue or the surrounding skin should be avoided, as well as those adjuvants which may react with and/or adversely reduce the effectiveness of the active ingredient which is incorporated within the film-forming carrier. Current Collodion-based FDA monograph approved formulas may be employed in such topical liquid compositions.

Preferably, in the method of this invention, the Collodion-based composition is applied to the scar tissue to be treated by any common applicator such as a brush, roll or eye dropping apparatus conveniently used to apply compositions to the skin. The compositions may also be applied by impregnating a porous base with the composition and wiping the composition onto the scar or where the porous base includes an adhesive, securing the porous base to the skin adjacent to the scar and wherein the film-former and active ingredient are placed on the scar to be treated. The composition used in the method of the present invention is a relatively viscous liquid which can be applied directly and accurately onto the scar tissue and does not require the application of additional pressure or rubbing as do certain oils and greases which have been previously utilized. Accordingly, it is believed that the use of the Collodion-based film-former with one or more medicaments to treat hypertrophic scars is novel.

In a second aspect of the present invention, a composition is provided to treat hypertrophic scars so as to reduce the size of the scars and improve the appearance thereof. In this aspect of the invention, an active ingredient in the form of a steroid is added to the Collodion-type film-forming carrier. Thus, it has been found that dermatologically active steroids which can be applied topically, such as hydrocortisone, betamethasone, and any other known corticosteroids and the like, as well as pharmaceutically acceptable salts thereof including chloride, acetate, etc., can be added to the Collodion film-forming carrier in amounts of from about 0.25% to about 70% by weight to yield a composition which can be readily and directly applied to the affected scar tissue. The composition dries to a clear film and maintains the steroid active ingredient in contact with the scar tissue and provides an advantageous and continuous healing effect of the steroid. As previously disclosed, adjuvants typically used for topical compositions can be added, including solvents, penetration enhancers, emollients, buffers, etc. as long as such addition does not adversely interfere with the effectiveness of the steroid.

The invention is further directed to a topical composition which can be used to readily and effectively treat a variety of adverse skin conditions including hypertrophic scars, eczema, psoriasis, atopic dermatitis, and other immunological skin disorders. In this aspect of the invention, topical actives such as steroids, including corticosteroids, silicone gels, i.e. non-volatile polysiloxanes, vitamins, including vitamins A and E, or mixtures thereof, are incorporated into a Collodion or Flexible Collodion film-forming carrier. The levels of each active component will vary depending on the skin disorder being treated and can be readily determined from known usages of the actives which have been contained in other carriers such as lotions, greases, oils or porous structures, e.g. bandages, gauze, etc. In general, levels of 0.25 wt. % to 75 wt. % are most practical but, variations are acceptable within the scope of this invention.

In still another aspect of the present invention, there is provided a composition which is useful to improve the size and appearance of hypertrophic scars. The composition again is based upon the Collodion-type film-forming carrier. In this aspect of the invention, three components which are active to improve hypertrophic scars and which have been used on an individual basis are now combined in the Collodion-type film-forming carrier which dries as a clear film on the affected area and provides a base in which the three components can act upon the scar tissue and provide the desired improvement. Thus, in accordance with this invention, the Collodion-type carrier has incorporated therein the dermatologically active steroid, a silicone gel and, optionally, vitamin E.

The dermatologically active steroid which can be used is that described above, in particular, corticosteroids such as hydrocortisone, betamethasone, and the like, including pharmaceutically acceptable salts thereof.

Additionally, it has been found that the Collodion-type carrier can still remain film-forming and a particularly advantageous composition can be formed by the further addition of silicone to the composition in addition to the dermatologically active steroid. The silicones which can be added to the composition of this invention are those which have been found effective to improve the appearance and size of hypertrophic scars. Silicones are a group of completely synthetic polymers containing the recurring group —$SiR_2O$— wherein R is a radical such as an alkyl, phenyl, or vinyl group which may be substituted or unsubstituted. The simpler silicones are oils of very low melting point, while at the other end of the scale of physical properties are highly cross-linked silicones which form rigid solids. Intermediate physical properties are silicone elastomers such as gels and rubbers. A variety of silicone gels have been used as wound dressings as disclosed in U.S. Pat. No. 4,838,253 assigned to Johnson and Johnson and U.S. Pat. No. 4,991,574 assigned to Dow. An example of a useful silicone gel which has been used is marketed under the tradename SILASTIC®.

While it has not been proven conclusively as to how the silicone gels act on the scar tissue to improve them, based on experiments involving the measurement of physical parameters associated with the use of such gels, investigators have concluded that the mode of operation of the silcone gel and scar treatment did not involve, pressure, temperature, oxygen, tension or occlusion. Rather, as reported, the likely mechanism involved both hydration of the stratum corneum and the release of a low molecular weight silicone fluid from the gel.

Any of the known silicone gels which have been previously used for wound dressings as described above can be used in the composition of this invention. In general, the silicone gel will have a viscosity at 25° C. of about 100–30,000 cps. Preferably, a phenyl trimethicone such as Dow Corning 556 fluid or a non-volatile polydimethylsiloxane can be used.

Although optional, it is preferred to include vitamin E (α-tocopherol) to the composition. In this most preferred embodiment, three active ingredients which have been known to treat hypertrophic scars on an individual basis have been found to be extremely useful in combined form in a single film-forming carrier without disadvantageous interactions between the components. Useful compositions can comprise from about 0.25–50% by weight of the steroid such as hydrocortisone, preferably from about 0.5–5% of the steroid; 2–70%, preferably 5–25% silicone and 0–25%, preferably 0.25–10% vitamin E. The balance is the Collodion-type film-forming carrier, whether Collodion or Flexible Collodion. Although the Collodion film-forming carrier is preferred, it is possible that other film-formers can be used. Examples include polyvinyl-pyrrolidone polymers and copolymers, polyacylate polymers and copolymers, etc.

As previously stated, other adjuvants can be added to enhance penetration of the active ingredients, control moisture levels on the scar tissue, provide preservative and antibacterial effects, etc. In a most preferred embodiment, small amounts of xanthan gum can be added which provides both thickening qualities and acts as a dispersion enhancer for the active ingredients, including the steroids such as hydrocortisone and the silicone component. If xanthan gum is added, it should be present in amounts of from about 0.5–4%, preferably from about 0.75–2.5% by weight.

The compositions of the present invention are believed to be novel. As the carrier system, the Collodion-type film-forming material containing the steroid and silicone has not been used to treat hypertrophic scars. While hydrocortisone is available as a topical ointment or cream and silicone is available as a liquid, an ointment or as a bandage sheet that must be cut and adhered to the skin with tape or other mechanism, the composition of the present invention combines these two active agents and disperses such agents into a matrix of an occlusive dressing that when brushed or otherwise applied onto the skin, dries immediately, keeps the active ingredients in contact with the skin to exert their intended action, and can easily be peeled off, either at completion of therapy or to apply subsequent doses. The compositions of this invention require no mechanical aid, i.e. adhesive bandage, gauze or impregnated sheet coverings. Application is simply accomplished by brushing the medicated viscous base onto the scar area and allowing to dry. The liquid base fully dries within one minute, creating a clear, flexible occlusive bandage covering. While the compositions can be easily brushed on, other applicators can be used including a dispensing-type device which will roll the material onto the scar, as well as eye dropper-type mechanisms. What is important, is that the carrier which contains the active ingredients of this invention does not need to be rubbed or massaged onto the scar area which can be painful in certain circumstances. Further, the carrier dries to a completely dry film which will not stick to clothing. Compositions of this invention have been found useful when applied once or twice daily for 3–4 months to yield the best results of softening, shrinking and lightening hypertrophic scars.

THE EXAMPLE

The following composition was prepared as a scar-healing composition and represents preferred embodiments of this invention. The composition was prepared by adding the ingredients shown to the carrier base, which in this instance was Flexible Collodion, USP.

10 wt. % silicone 556
1 wt. % hydrocortisone hydrochloride
0.5% a.pha-tocopherol (vitamin E)
1.2 wt. % xanthan gum
balance of Flexible Collodion, USP The Example is not intended to strictly limit the invention to the embodiments shown. It should be understood that the foregoing detailed description is given merely by way of illustration. obviously, many modifications and variations of the invention as hereinbefore set forth can be made without departing from the spirit and scope thereof, and therefore, only such limitations should be imposed as are indicated by the appended claims.

What is claimed is:

1. A method of treating hypertrophic scars so as to reduce the size and/or improve the appearance thereof comprises; applying onto a hypertrophic scar a liquid composition comprising a Collodion film-forming carrier having contained therein a dermatologically effective amount of an active ingredient capable of reducing the size of the scar or improving the appearance thereof, drying said film-forming carrier to form a dry protective film physically adhered to said scar to maintain contact of the active ingredients on said scar.

2. The method of claim 1 wherein the Collodion film-forming carrier comprises Collodion or Flexible Collodion.

3. The method of claim 1 wherein said liquid composition is applied onto the scar by brushing, rolling or applying drops of said composition onto the scar.

4. The method of claim 3 wherein said liquid composition is applied to the scar by brushing.

5. The method of claim 1 wherein said active ingredient comprises at least one of a topical steroid, silicone gel, or vitamin.

6. The method of claim 5 wherein said active ingredient includes hydrocortisone or a pharmaceutically acceptable salt thereof.

7. The method of claim 5 wherein said active ingredient comprises a combination of a topical steroid and silicone gel.

8. The method of claim 7 wherein said topical steroid is hydrocortisone or a pharmaceutically acceptable salt thereof.

9. The method of claim 7 wherein said composition further includes vitamin E.

10. The method of claim 5 wherein said active ingredient is a corticosteroid.

11. A composition for treating adverse skin conditions comprising a liquid Collodion film-forming carrier and a dermatologically effective amount of an active ingredient comprising a topically active steroid, silicone gel, vitamins or mixtures of said active ingredients, wherein said liquid carrier is capable of drying to a dry protective film physically adhered to skin and containing said active ingredient.

12. The composition of claim 11 wherein said active ingredient is a topically active steroid comprising hydrocortisone or a pharmaceutically acceptable salt thereof.

13. The composition of claim 11 wherein said active ingredient is a silicone gel.

14. The composition of claim 13 wherein said silicone gel is phenyltrimethicone.

15. The composition of claim 11 wherein said active ingredient comprises vitamin E.

16. The composition of claim 11 wherein said active ingredient comprises a mixture of a topical steroid, a silicone gel, and optionally, vitamin E.

17. The composition of claim 16 wherein said topical steroid is hydrocortisone or a pharmaceutically acceptable salt thereof and said silicone gel has a viscosity at 25° C. of 100–30,000 centipoises.

18. The composition of claim 17 wherein said silicone gel comprises phenyltrimethicone.

19. The composition of claim 16 wherein said film-forming carrier is Collodion or Flexible Collodion.

20. The composition of claim 11 wherein said active ingredient is a corticosteroid.

21. A composition to reduce the size and improve the appearance of hypertrophic scars comprising a dermatologically effective amount of mixture of a topical steroid and silicone gel in a liquid film-forming carrier, said carrier capable of drying to a dry protective coating film containing said mixture and physically adhered to the surface of the scar.

22. The composition of claim 21 further including vitamin E.

23. A dry bandage covering consisting essentially of a dried film-forming liquid collodion composition having contained therein a dermatologically effective amount of corticosteroid.

24. The bandage of claim 23 further containing a silicone gel or vitamin or mixtures thereof.

* * * * *